US006629469B2

(12) United States Patent
Jaszczak et al.

(10) Patent No.: US 6,629,469 B2
(45) Date of Patent: Oct. 7, 2003

(54) CARDIAC PHANTOM

(75) Inventors: Ronald J. Jaszczak, Chapel Hill, NC (US); Paul Douglas Kirven, Durham, NC (US); Timothy Warren Perry, Hillsborough, NC (US)

(73) Assignee: Data Spectrum Corporation, Hillsborough, NC (US)

( * ) Notice: Subject to any disclaimer, the term of this patent is extended or adjusted under 35 U.S.C. 154(b) by 0 days.

(21) Appl. No.: 09/874,582

(22) Filed: Jun. 5, 2001

(65) Prior Publication Data

US 2002/0178845 A1 Dec. 5, 2002

Related U.S. Application Data

(60) Provisional application No. 60/209,520, filed on Jun. 5, 2000.

(51) Int. Cl.[7] .............................................. G01M 19/00
(52) U.S. Cl. .................................................... 73/866.4
(58) Field of Search ........................ 73/866.4; 434/268, 434/272, 267, 269

(56) References Cited

U.S. PATENT DOCUMENTS

| 3,208,448 A | 9/1965 | Woodward ...................... 128/1 |
| 3,597,766 A | 8/1971 | Buck ................................. 3/1 |
| 3,955,088 A | 5/1976 | Muehllehner et al. ... 250/363 S |
| 4,014,109 A | 3/1977 | Schramm ....................... 35/17 |
| 4,057,726 A | 11/1977 | Jaszczak ..................... 250/363 |
| 4,280,047 A | 7/1981 | Enos .......................... 250/252 |
| 4,331,869 A | 5/1982 | Rollo .......................... 250/252 |
| 4,499,375 A | 2/1985 | Jaszczak ..................... 250/252 |
| 4,719,406 A | 1/1988 | Schaefer et al. ............. 324/318 |
| 4,818,943 A | 4/1989 | Chandra ..................... 324/318 |
| 4,894,013 A | 1/1990 | Smith et al. ................. 434/268 |
| 4,974,461 A | 12/1990 | Smith et al. ................ 73/865.6 |
| 5,052,934 A * | 10/1991 | Carey et al. ................. 434/268 |
| 5,289,008 A | 2/1994 | Jaszczak et al. ........ 250/363.03 |
| 5,312,755 A | 5/1994 | Madsen et al. ................. 436/8 |
| 5,528,944 A * | 6/1996 | Hoyt et al. ................. 73/866.4 |
| 5,632,623 A * | 5/1997 | Kolff et al. .................. 434/272 |
| 5,756,875 A | 5/1998 | Parker et al. .............. 73/1 DV |
| 6,205,871 B1 | 3/2001 | Saloner et al. ............. 73/866.4 |

FOREIGN PATENT DOCUMENTS

| DE | 4233365 | 4/1994 | ............ A61B/6/03 |
| DE | 4233365 A1 * | 4/1994 | ............ A61B/6/10 |
| FR | 2708775 | 2/1995 | ........... G09B/23/28 |
| FR | 2708775 A1 * | 2/1995 | ........... G09B/23/28 |

OTHER PUBLICATIONS

A. Nowicki, R. Olszewski, J. Etienne, p. Karlowicz, and J. Adamus, "Assessment Of Wall Velocity Gradient And Thrombi Detection Using Test–Phantom", IEEE Proceedings Ultrasonics Symposium, Nov. 1996, pp. 1189–1191.

(List continued on next page.)

Primary Examiner—Daniel S. Larkin
Assistant Examiner—Charles D Garber
(74) Attorney, Agent, or Firm—Moore & Van Allen PLLC; Michael G. Johnston

(57) ABSTRACT

A cardiac phantom is provided for simulating a dynamic cardiac ventricle. The phantom comprises two concentrically-disposed, fluid-tight, flexible membranes defining a closed space between the walls of the membranes. A pump is operatively connected to the inner membrane for reciprocally delivering a volume of fluid to the inner membrane to inflate and deflate both membranes in simulating systole and diastole of a heart. A medium is disposed within the closed space defined between the walls of the membranes for maintaining a uniform distance between the walls of the membranes during inflation and deflation. The phantom is provided for evaluation of medical imaging systems. A method, computer system and a computer-readable medium are also provided for controlling the phantom.

19 Claims, 10 Drawing Sheets

OTHER PUBLICATIONS

A. Millaire, J. Rousseau, G. Ducloux, and X. Marchandise, "A Dynamic And Asymmetric Phantom For Left Ventricular Regional Wall Motion Assessment", Engineering In Medicine And Biology Society, Sep. 1995, pp. 143–144.

M.L.J. Rose, G.A. Wright, T.G. Mackay, W. Martin, and D.J. Wheatley, "Correlation of radionuclide and optical tracer assessments of fluid flow in artificial ventricles", Physiological Measurement, IOP Publishing, GB, vol. 18, No. 3, Aug. 1997, pp. 171–182.

Ronald J. Jaszczak, R. Edward Coleman, and Chun Bin Lim, "SPECT: Single Photon Emission Computed Tomography", pp. 1137–1153, Jun. 1980, IEEE Transactions on Nuclear Science.

Osman Ratib, Eberhard Henze, Edward Hoffman, Michael E. Phelps, and Heinrich R. Schelbert, "Performance of the Rotating Slant–Hole Collimator for the Detection of Myocardial Perfusion Abnormalities", pp. 34–41, Aug. 1981, The Journal of Nuclear Medicine.

Wei Chang, Sheng Ling Lin, and Robert E. Henkin, "A New Collimator for Cardiac Tomography: The Quadrant Slant–Hole Collimator", pp. 830–835, Sep. 1982, The Journal of Nuclear Medicine.

M.J. Myers, E. Busemann Sokole, and J. de Bakker, "A comparison of rotating slant hole collimator and rotating camera for single photon emission tomography of the heart", pp. 581–588, Dec. 1981, The Institute of Physics.

R. Edward Coleman, MD, Russell A. Blinder, MD, and Ronald J. Jaszczak, PhD, "Single Photon Emission Computed Tomography (SPECT) Part II: Clinical Applications", pp. 1–11, Jan. 1986, Investigative Radiology.

Theodore R. Simon, Brandy S. Walker, Sharon Matthiesen, Charles Miller, Jeffrey G. Triebel, J. Edward Dowdey, and Thomas C. Smitherman, "A Realistic Dynamic Cardiac Phantom for Evaluating Radionuclide Ventriculography: Description and Initial Studies with the Left Ventricular Chamber", pp. 542–547, Apr. 1989, The Journal of Nuclear Medicine.

Jorg F. Debatin, MD, Scott N. Nadel, MD, H. Dirk Sostman, MD, Charles E. Spritzer, MD, Avery J. Evans, MD, and Thomas M. Grist, MD, "Magnetic Resonance Imaging–Cardiac Ejection Fraction Measurements", pp. 198–204, Mar. 1992, Investigative Radiology.

R.J. Jaszczak, D.R. Gilland, M.W. Hanson, S. Jang, K.L. Greer and R.E. Coleman, "Fast Transmission CT for Determining Attenuation Maps Using a Collimated Line Source, Rotatable Air–Copper–Lead Attenuators and Fan–Beam Collimation", pp. 1577–1586, Sep. 1993, Journal of Nuclear Medicine.

Sunyoung Jang, Ronald J. Jaszczak, Jianying Li, Jorg F. Debatin, Scott N. Nadel, Avery J. Evans, Kim L. Greer, and R. Edward Coleman, "Cardiac Ejection Fraction and Volume Measurements Using Dynamic Cardiac Phantoms and Radionuclide Imaging", pp. 2845–2849, Dec. 1994, IEEE Transactions on Nuclear Science.

VAAST Company Brochure, 2 pages, Aug. 1996.

Wei Chang and Robert E. Henkin, "Photon Attenuation In Tl–201 Myocardial Spect And Quantitation Through An Empirical Correction", pp. 1–11, Society of Nuclear Medicine.

* cited by examiner

CARDIAC PHANTOM

RELATED APPLICATIONS

This application claims the benefit of U.S. provisional patent application No. 60/209,520, filed Jun. 5, 2000.

BACKGROUND

This invention relates generally to a medical imaging phantom, and more particularly to a cardiac phantom for use in medical imaging for diagnostic purposes.

A number of different nuclear imaging instruments have been devised for diagnosing patient aliments and conditions. The field of use of such instruments is known as the field of nuclear medicine. Nuclear imaging instruments are advantageous in that they can produce images of conditions within soft tissue organs of a patient's body without exploratory surgery.

In the practice of nuclear medicine, a low level of a tracer radioisotope is injected into a patient. The tracer radioisotope is carried in the patient's bloodstream to the patient's internal organs, such as the heart, liver, kidneys, or brain. The tracer radioisotope emits gamma rays, a portion of which pass from the patient's body and are detectable by nuclear imaging instruments and reflect, for example, blood flow or metabolic function in the organ.

In order to calibrate and check the accuracy of nuclear imaging instruments, test structures, known in the field as phantoms, are utilized. Other prior nuclear imaging phantoms have been produced in forms which encase radioactive sources within a structure which simulate the shape and gamma ray attenuation properties of the human body. Such conventional test phantoms may employ concentrated radioactive sources which are imaged as "hot" spots or small non-radioactive structures within a homogenous radioactive source which exhibit "cold" spots in the image produced. The nuclear imaging instruments are used to produce images of the phantom. By examining the images produced, the degree to which the image conforms to the actual phantom structure and the degree to which irregularities exist in the image are ascertained.

Nuclear imaging is a common non-invasive technique used in the evaluation of cardiac function and disease. Left ventricular ejection fraction and volume measurements are central to the objective characterization of cardiac performance. They are widely used as prognostic and therapeutic indicators in patients with different cardiac diseases. The importance of the measurement of the left ventricular ejection fraction and volume has been well recognized. Thus, the accuracy of the ejection fraction measurement and volume estimation performed by nuclear imaging devices with dynamic cardiac phantoms is important.

Conventional cardiac phantoms of various sorts have been used extensively to study and validate measurements by nuclear and other medical imaging devices. Left ventricular models and casts have served as primary reference standards to validate imaging methods. However, cardiac phantoms are limited in applicability because they are static, or not anatomically realistic in shape. In particular, past cardiac phantoms have been particularly inadequate in simulating a beating heart. Moreover, substantial problems still complicate accurate measurements of left ventricular contractility. Realistic, expansible phantoms of the left ventricle to simulate the left ventricle of the beating heart are needed for use in left ventricular ejection fraction and volume measurement under various simulated clinical conditions.

For the foregoing reasons, there is a need for a new, more realistic cardiac phantom. Specifically, the new phantom should be a beating phantom which allows real time nuclear imaging. In particular, the new phantom should allow medical imaging and measurement of the left ventricular region during all phases of the heart action.

SUMMARY

According to the present invention there is provided an apparatus for simulating a dynamic cardiac ventricle. The apparatus comprises two concentrically-disposed, fluid-tight, flexible membranes defining a closed space between the walls of the membranes. A pump is operatively connected to the inner membrane for reciprocally delivering a volume of fluid to the inner membrane to inflate and deflate both membranes in simulating systole and diastole of a heart. A medium is disposed within the closed space defined between the walls of the membranes for maintaining a uniform distance between the walls of the membranes during inflation and deflation.

Also according to the present invention, a phantom is provided for evaluation of a medical imaging system. The phantom comprises a closed container of fluid and a simulated dynamic cardiac ventricle disposed within the container. The simulated cardiac ventricle includes two concentrically-disposed, fluid-tight, flexible membranes defining a closed space between the walls of the membranes and a medium disposed within the closed space defined between the walls of the membranes for maintaining a uniform distance between the walls of the membranes during inflation and deflation. A fluid delivery system including a pump between the container of fluid and the inner membrane provides a reciprocating volume of fluid between the container and the inner membrane to inflate and deflate both membranes in simulating systole and diastole of a heart.

Further according to the present invention, a method is provided for controlling an apparatus capable of simulating a cardiac ventricle. The method comprises the steps of determining data points for a ventricular volume versus time curve, sampling a position of a pump motor, determining the pump motor position and at least one subsequent position of the pump motor corresponding to the volume versus time curve, calculating velocity and acceleration to reach the subsequent position to simulate a cardiac ventricle, and moving the pump motor to the subsequent position based on the calculated velocity and acceleration.

A computer system is also provided according to the present invention for controlling an apparatus capable of simulating a cardiac ventricle. The computer system comprises means for determining data points for a ventricular volume versus time curve, means for sampling a position of a pump motor, means for determining the pump motor position and at least one subsequent position of the pump motor corresponding to the volume versus time curve, means for calculating velocity and acceleration to reach the subsequent position to simulate a cardiac ventricle, and means for moving the pump motor to the subsequent position based on the calculated velocity and acceleration.

Still further according to the present invention, a computer-readable medium is provided. The contents of the medium cause a computer system to control an apparatus capable of simulating a cardiac ventricle by performing the steps of determining data points for a ventricular volume versus time curve, sampling a position of a pump motor, defining the pump motor position and at least one subsequent position of the pump motor corresponding to the volume versus time curve, calculating velocity and acceleration to reach the subsequent position to simulate a cardiac ventricle, and moving the pump motor to the subsequent position based on the calculated velocity and acceleration.

BRIEF DESCRIPTION OF DRAWINGS

For a more complete understanding of the present invention, reference should now be had to the embodiments shown in the accompanying drawings and described below. In the drawings.

DESCRIPTION

Certain terminology used herein for convenience only is not to be taken as a limitation of the invention. For example, words such as "upper", "lower", "left", "right", "horizontal", "vertical", "upward" and "downward" merely describe the configuration shown in the figures. Indeed, the components may be oriented in any direction. Therefore, the terminology should be understood as encompassing such variations unless specified otherwise.

Figure 1:
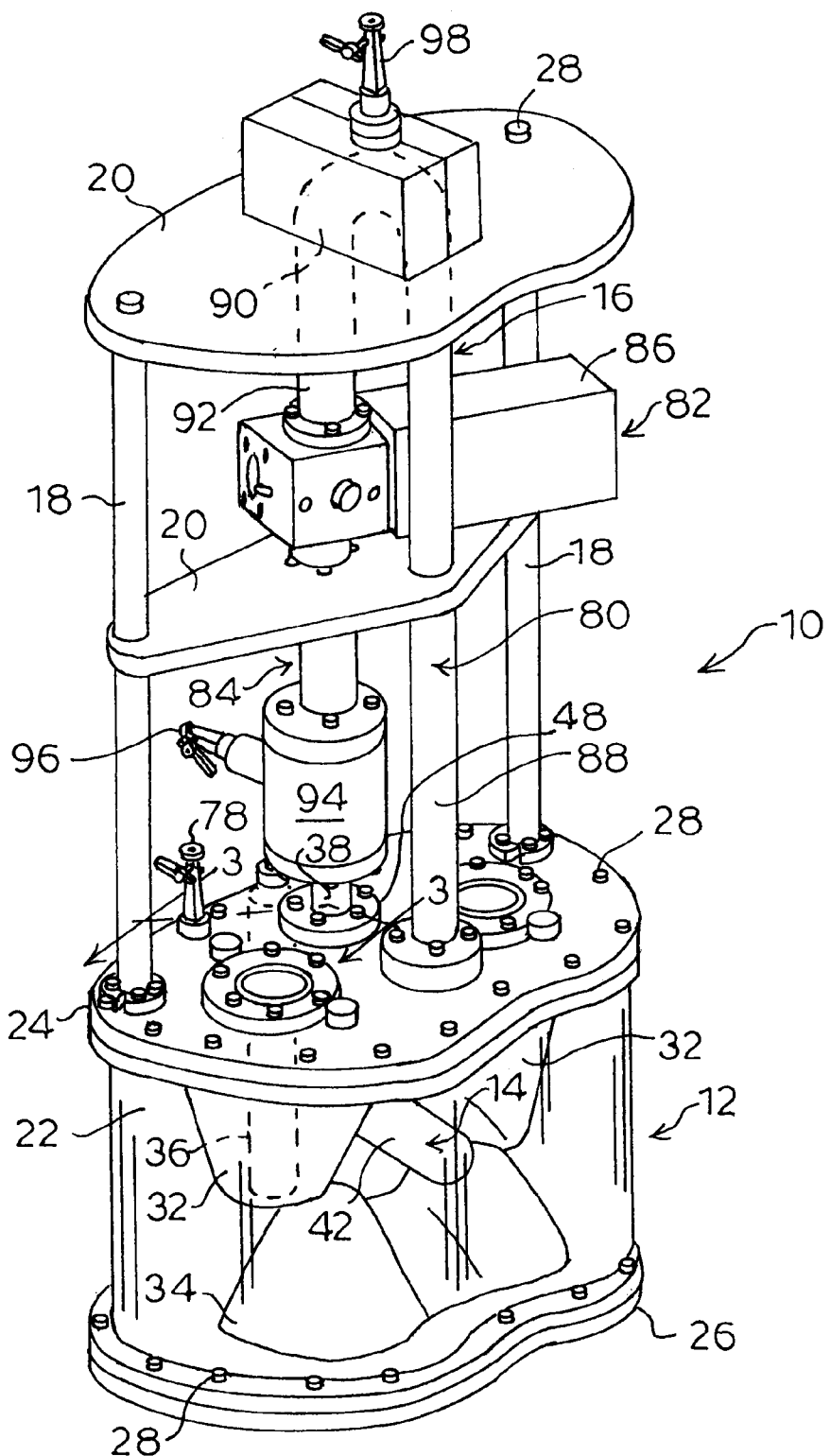
FIG. 1 is a perspective view of an embodiment of a cardiac phantom according to the present invention.
Figure 2:
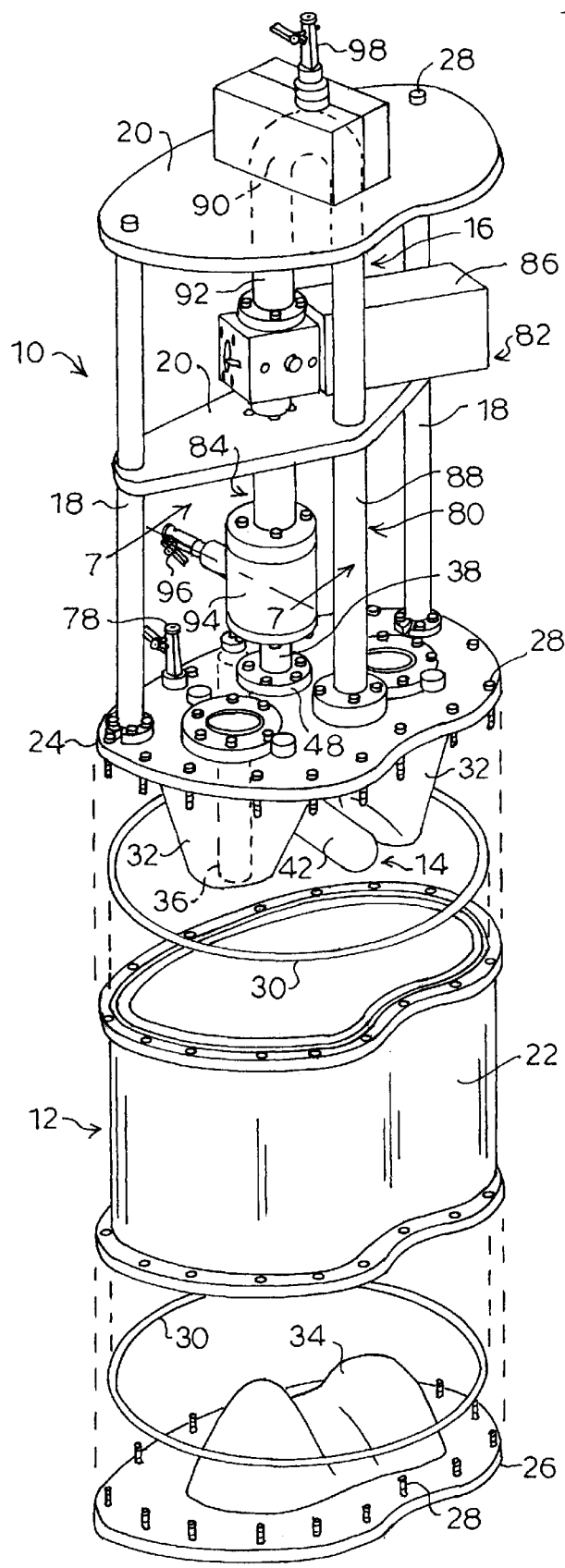
FIG. 2 is an exploded perspective view of the cardiac phantom shown in FIG. 1.

Referring now to the drawings wherein like reference numerals designate corresponding or similar elements throughout the several views, FIGS. 1 and 2 show an apparatus for use as a cardiac phantom according to the present invention and generally designated at 10. The cardiac phantom 10 comprises a thoracic portion 12 housing a left ventricular assembly 14 and a fluid delivery system 16 mounted to a support structure 18. The support structure 18 comprises two generally horizontal plates 20 and a plurality of vertical support members 22 extending upwardly from the top surface of the thoracic portion 12.

The thoracic portion 12 comprises a fluid tight elliptical cylinder. In one embodiment of the present invention, the thoracic portion 12 is a thoracic phantom including an acrylic tank 22, a top plate 24 and a bottom plate 26. The top plate 24 and bottom plate 26 are fastened to the tank 22 using threaded fasteners 28. Only the fasteners 28 for the top plate 24 are shown in FIG. 2. O-rings 30 are positioned between the plates 24, 26 and tank 22 to seal the interface between the edges of the tank 22 and the plates 24, 26 against fluid leakage. The thoracic phantom is designed to account for the low density and complex tissue distribution in the thorax. Accordingly, forms representing, for example, the lungs 32 and liver 34 within a human torso are integral with or mounted to the tank 22 wall and extend into the tank. The two lung inserts 32 may contain tightly-packed Styrofoam beads and are filled with water to simulate the density of lung tissue. Other pseudo-anatomic features may be built into the thoracic phantom simulating the spine 36, the sternum (not shown), back muscles (not shown) and the like. A suitable thoracic phantom for use in the present invention is available from Data Spectrum Corporation, Hillsborough, N.C., under the name Anthropomorphic Torso Phantom, Model ECT/TOR/P.

Figure 3:
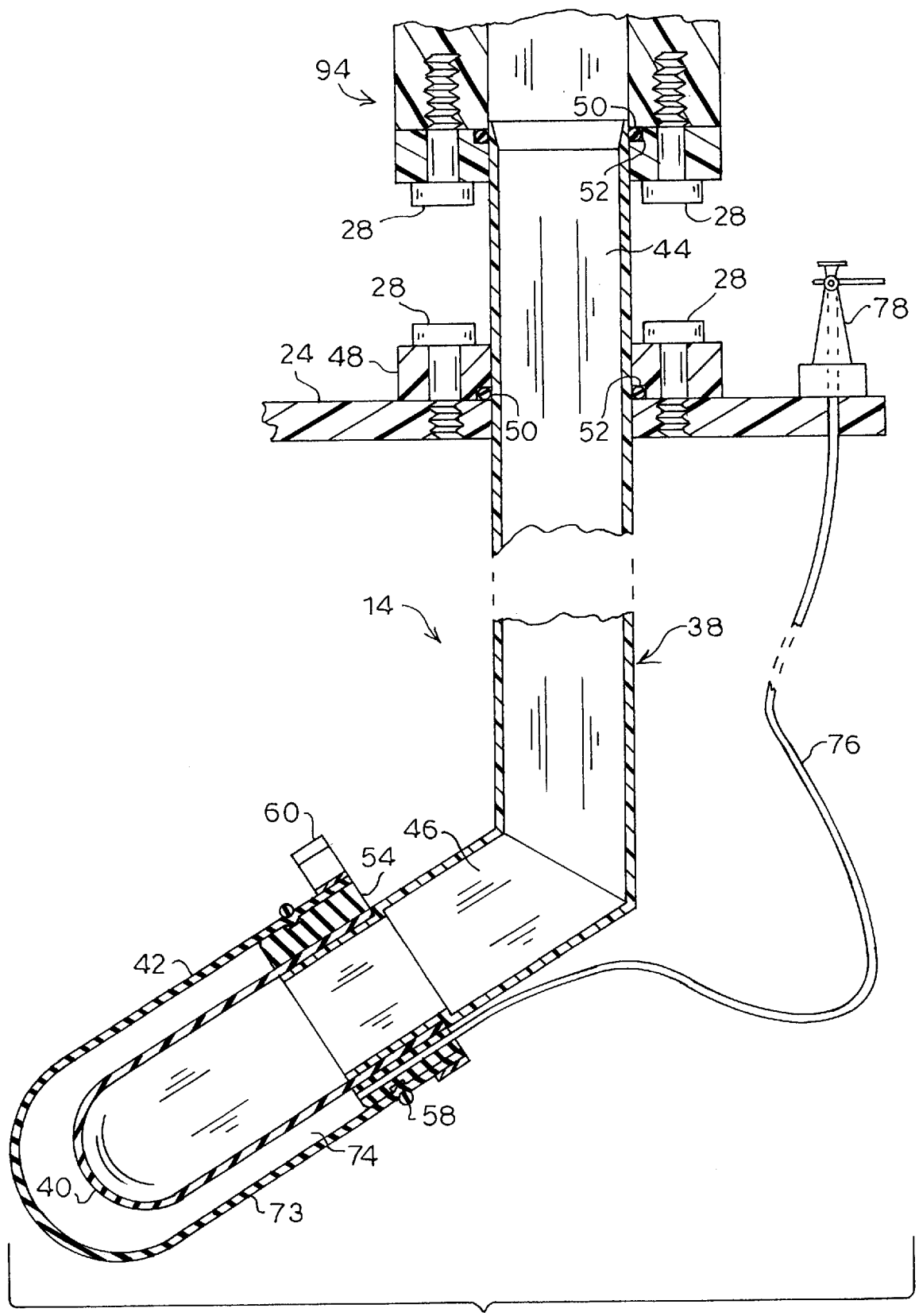
FIG. 3 is a sectional view of a left ventricular portion of an embodiment of the cardiac phantom according to the present invention.
Figure 4:
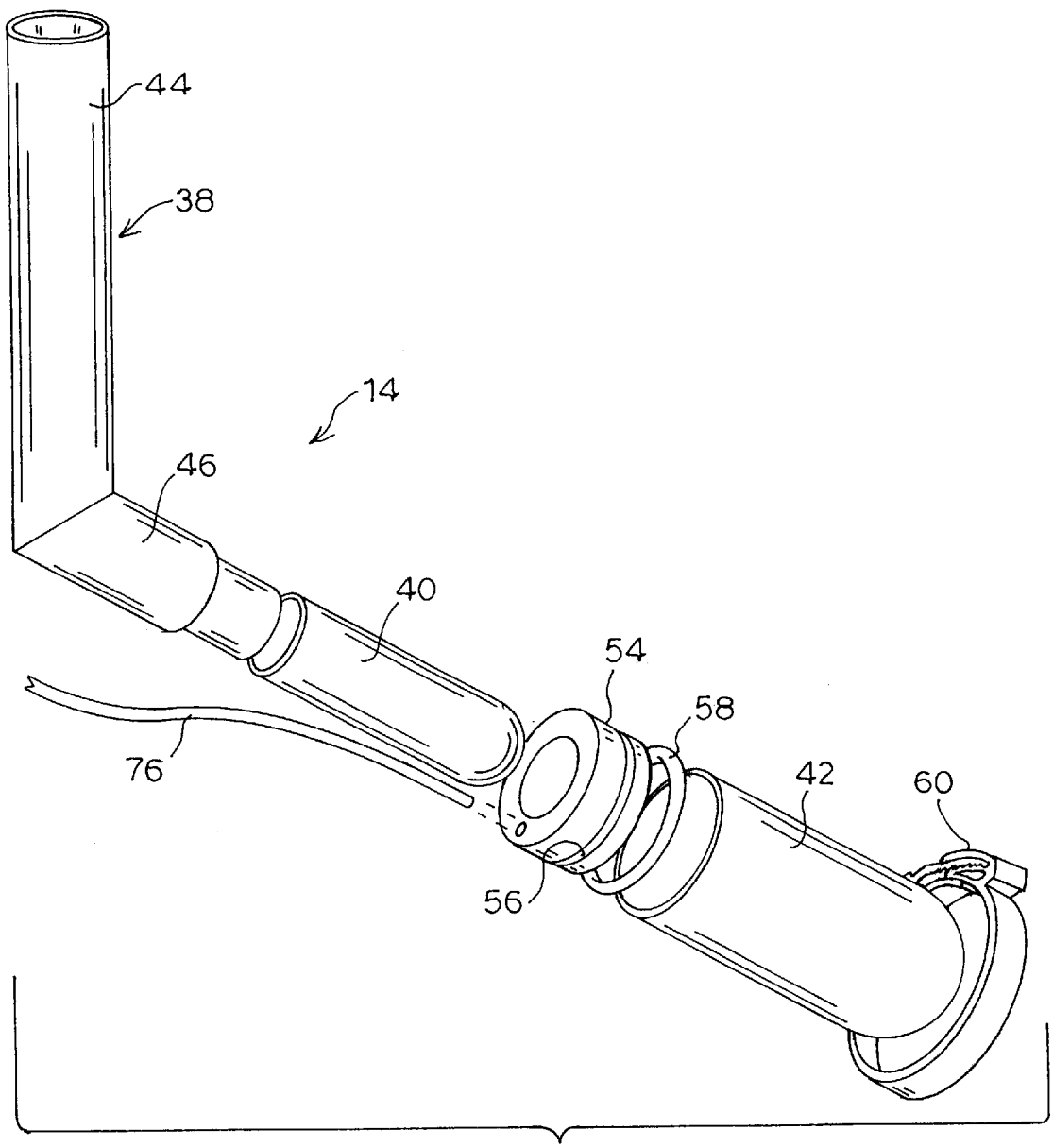
FIG. 4 is an exploded view of the left ventricular portion of the cardiac phantom shown in FIG. 4.

The left ventricular assembly 14, partially visible in FIGS. 1 and 2, is shown in detail in FIGS. 3 and 4. The left ventricular assembly 14 comprises a fluid delivery tube 38, an inner tubular cap member 40 and an outer tubular cap member 42. The fluid delivery tube 38 has an upper portion 44 and a lower portion 46. The upper portion 44 of the fluid delivery tube 38 extends vertically through an opening in the top plate 24 of the thoracic portion 12. As seen in FIG. 3, the opening in the top plate 24 is sealed using a close-fitting flange 48 and an o-ring 50. The lower surface of the flange 48 has an annular groove 52 which receives the o-ring 50. The flange 48 is secured against the top surface of the top plate 24 using threaded fasteners 28. As the fasteners 28 are tightened, the o-ring 50 is pressed against the outer surfaces of the top plate 24 and fluid delivery tube 38 for sealing the interface. It is understood that all connections in the thoracic portion 12 and fluid delivery system 16 of the present invention may be sealed using this flange 48 and o-ring 50 arrangement. The lower portion 46 of the fluid delivery tube 38 forms an angle of between about 15 and about 30 degrees with the upper portion 44 to approximate the orientation of the heart in the chest cavity when the left ventricular phantom 14 is freely suspended from the end of the lower portion 46 of the fluid delivery tube, as seen in FIGS. 1 and 2.

As best seen in FIG. 4, the tubular cap members 40, 42 are ellipsoid-shaped. The cap members 40, 42 are formed from flexible, resilient material allowing them to expand and contract like the heart muscle. In one embodiment, the cap members are latex balloons. The latex balloons are formed by preparing a solution by dissolving 50 parts of calcium nitrate tetrahydrate in 50 parts reagent alcohol. A latex dipping bath is also prepared by adding a wetting agent (0.1–0.25 pphr) and an antioxidant (1.0–3.0 pphr) to a pre-vulcanized, natural rubber latex. Aqueous dispersions of surfactants are acceptable as wetting agents, such as sodium lauryl sulphate, potassium oleate, or Darvan WAQ available from R. T. Vanderbilt Co., Inc., of Norwalk, Conn. and Octowet 70D available from Tiarco Chemical Co., of Dalton, Ga. Satisfactory aqueous dispersions of antioxidants of the non-discoloring, hindered-phenolic type include Octolite 640 available from Tiarco Chemical Co., Bostex 24 available from Akron Dispersions of Akron, Ohio, Akrosperse W-19119 available from Akrochem Corp. of Akron, Ohio, and Agerite Superlite available from R. T. Vanderbilt Co., Inc. The latex is a medium modulus, pre-vulcanized natural rubber latex such as Guthrie PVMM from Guthrie Latex, Inc. of Tucson, Ariz., Chemionics-960CX9949 from Chemionics Corp. of Tallmadge, Ohio, and Heveatex HA-1438/D710 from Heveatex Corp. of Fall River, Mass. The preferred components are Darvan WAQ, Agerite Superlite and Guthrie PVMM. Distilled water is added to the latex dipping bath until the total solids content is 55%. The compounded latex is matured at room temperature for about 48 hours, then filtered through a stainless steel 80-mesh sieve.

A ventricle-shaped, aluminum former is heated in air at about 70° C. for 30 minutes, dipped in the prepared solution for less than about 10 seconds, then dried in air at room temperature for 15 minutes leaving the former coated with a uniform gel of coacervant. The former is heated to facilitate solvent evaporation. The coated former is submerged in the latex dipping bath where it remains dwelled for about 5 to about 10 minute. The former is withdrawn from the latex at a rate of 1–2 mm per second. The resulting opaque, rubber gel is dried in air at about 21–23° C. for up to about 30 minutes. The former is leached in distilled water at about 40° C. to about 50° C. for 2 to 3 hours to remove non-rubber constituents and then dried in air at 50° C. for several hours until the rubber cap material becomes transparent. The cap material is then wet-stripped from the former, leached in distilled water at 30° C. for up to 24 hours to further remove remaining hydrophilic materials, then dried in air at 50° C. for several hours until transparency is restored. Finally, the cap member is surface-treated by immersion in an aqueous chlorine solution (0.40 g Cl⁻/L water) at 21–23° C. for up to about 30 minutes. The cap member may optionally be neutralized in a KOH/water solution (pH=8.5) at 21–23° C. for 5 minutes. In either case, the cap member is rinsed in water at 21–23° C. for about 10 minutes, then dried in air at about 50° C. to about 70° C. for up to about 30 minutes. The resulting cap member is transparent, amber, glossy, and tack-free.

Referring to FIGS. 3 and 4, the distal end of the lower end portion 46 of the fluid delivery tube 38 has a reduced diameter for receiving the open end of the inner cap member 40. A rubber collar 54 fits snugly over the end of the tube 46 and cap 40. The outer cap member 42 then slips over the collar 54. The collar 54 has a circumferential groove 56 for receiving an o-ring 58 which fits over the outer cap member 42 and helps seal the outer cap member against the collar 54. Finally, a clamp 60 is secured around the whole arrangement providing a fluid tight seal.

Figure 5:
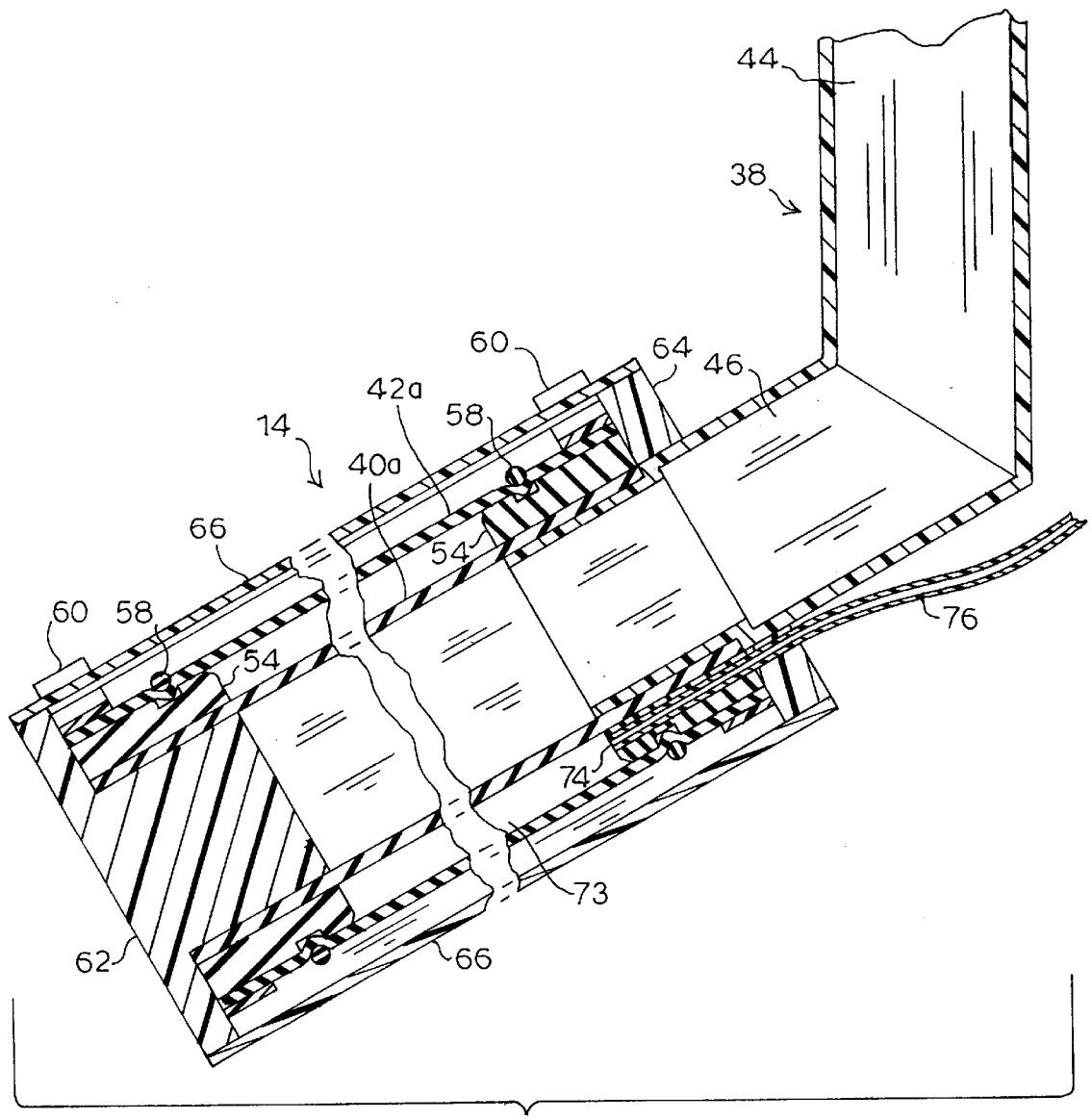
FIG. 5 is a sectional view of another embodiment of a left ventricular portion of the cardiac phantom according to the present invention.

Another embodiment of the left ventricular assembly, generally designated at 14a, is shown in FIG. 5. In this embodiment, the inner cap member 40a and outer cap member 42a are open-ended. The cap members 40a, 42a may be formed from latex in the same manner as described above with the additional step of removing the closed ends. The upper ends of the cap members 40a, 42a are secured on the end of the lower portion 46 of the fluid delivery tube 38 in the same manner as described above in the previous embodiment. The lower free end of the inner cap member 40a fits snugly over a smaller diameter end of a headed plug 62. The remainder of the structure at the lower free ends of the cap members 40a, 42a is the same as at the upper end, including a rubber collar 54, o-ring 58 and clamp 60. In this embodiment, a longitudinal guide assembly is also provided, comprising a ring 64 and at least one longitudinal guide member 66. The ring 64 is secured on the lower portion 46 of the fluid delivery tube 38 adjacent the reduced diameter end. The guide members 66, in one embodiment, are arcuate plates fastened at one end to the ring 64 and extending longitudinally from the ring at least to the head of the plug 62. The guide members 66 may optionally be secured to the head of the plug 62. This arrangement provides support to and guides the movement of the cap members 40a, 42a.

Figure 6:
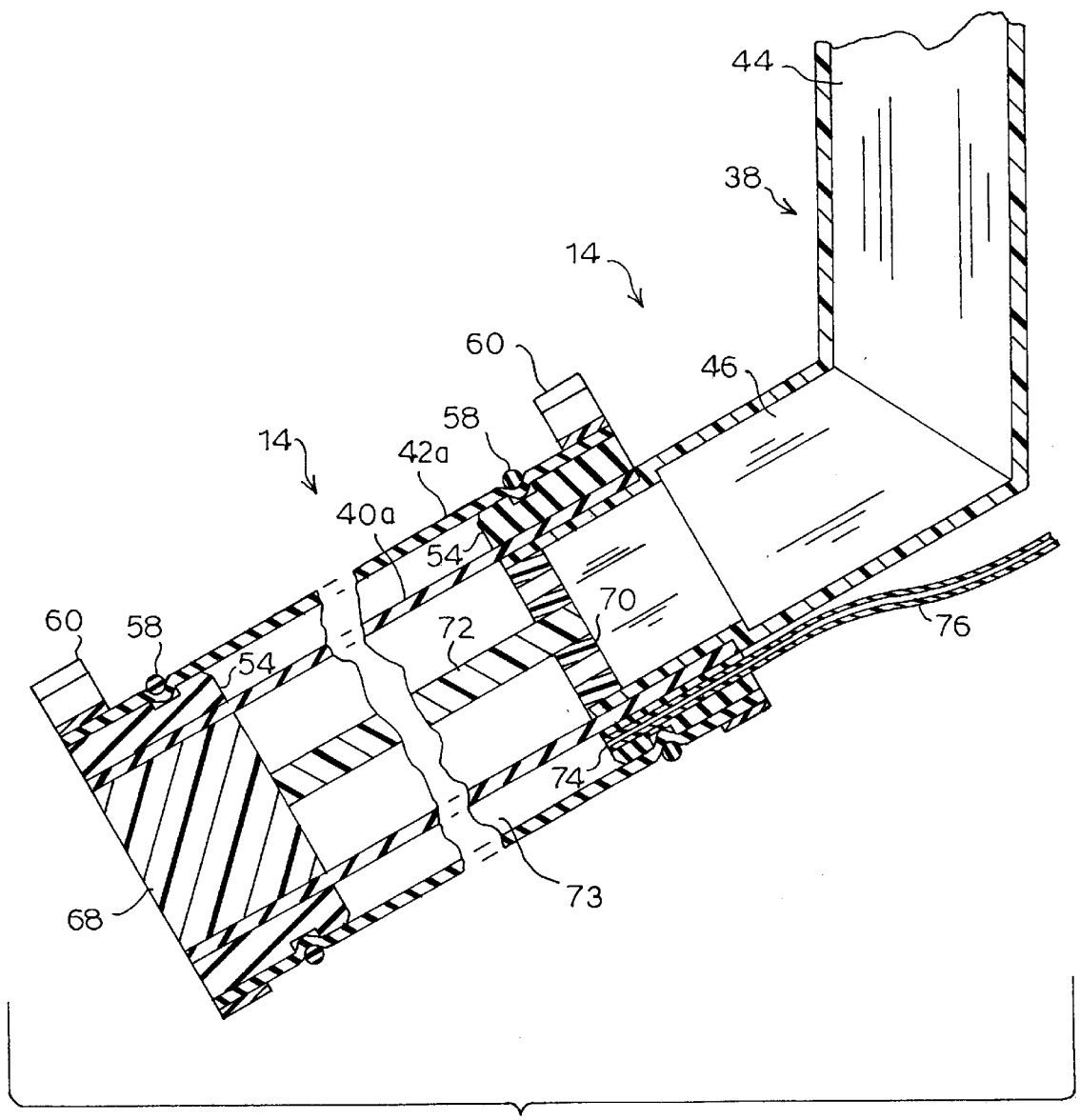
FIG. 6 is a sectional view of still another embodiment of a left ventricular portion of the cardiac phantom according to the present invention.

Still another embodiment of the left ventricular assembly, generally designated 14b, is shown in FIG. 6. In this embodiment, the inner cap member 40a and outer cap member 42a are also open-ended. The upper ends of the cap members 40a, 42a are secured on the end of the lower portion 46 of the fluid delivery tube 38 in the same manner as described above in the previous two embodiments. The lower free end of the inner cap member 40a fits snugly over the end of a plug 68 which fits inside the end of the inner cap member 40a. The remainder of the structure at the lower free ends of the cap members 40a, 42a is the same as at the upper end, including a rubber collar 54, o-ring 58 and clamp 60. In this embodiment, a disc 70 is secured inside the lower portion 46 of the fluid delivery tube 38. The disc 70 has a plurality of openings to allow fluid to pass. A rod 72 a secured at the ends between the plug 68 and the disc 70. The rod 72 provides support to the cap member assembly. In one embodiment, the rod 72 may be hollow and adapted to hold fluid, such as water or active solution for imaging.

As seen in FIGS. 3, 5 and 6, a space 73 is defined between the outer surface of the inner cap member 40, 40a and the inner surface of the outer cap member 42, 42a. A longitudinal passage 74 is provided in the collar 54. One end of a fluid line 76 fits into the passage 74 in the collar 54 and the other end of the fluid line 76 is attached to a fluid valve 78 mounted to the top plate 24. The valve 78 allows the user to add water or active solution to the space 73 between the walls of the cap members 40, 40a, 42, 42a. The space 73 represents the myocardium of the heart. The range of thickness of the space is adapted during expansion and contraction of the cap members to simulate the range of the left ventricular myocardial thickness usually encountered in clinical conditions.

Another means for controlling the thickness and shape of the simulated myocardial wall is to use a layer of solid material such as foam, and in one embodiment an open-cell foam. The layer of foam is formed to the desired shape and thickness (about 1 cm.) of the myocardium. An adhesive is used to attach the outer surface of the inner cap member 40, 40a and the inner surface of the outer cap member 42, 42a to the inner and outer surfaces, respectively, of the myocardium-shaped foam. Alternatively, the foam myocardium could be made slightly thicker than the distance between the cap members 40, 40a, 42, 42a. In this case, the foam would be self-positioning and no adhesive would be needed. In either embodiment, the foam has sufficient stiffness to provide adequate control of the thickness of the myocardial wall, yet be flexible enough to respond to the pump 84 of the fluid delivery system 16 to produce the desired ventricular volume curve, as will be described below. The foam returns to its original shape after thousands of "beating heart" cycles. The foam can also be shaped to simulate a defect of the heart. In one embodiment, the cells of the open-cell foam are of sufficient size so that liquid, radioactive tracer material can freely flow into and out of the foam.

Referring now to FIGS. 1 and 2, the fluid delivery system 16 comprises tubing 80 and a pump assembly 82 including a pump 84 and motor 86. The tubing 80 is formed of rigid acrylic material. The tubing 80 is rigid so that the tubing does not effect the transmission of the volume of fluid in the system 16. The tubing 80 includes a front vertical portion 88 passing through the intermediate plate 20 and a curved crossover portion 90 joined to upper end of the front vertical portion 88 thereby approximating a j-shape. The lower end of the front vertical portion 88 opens into the thoracic portion 12 and is secured to the top plate 24 in a fluid tight manner, using a flange 48 and o-ring 50 arrangement as described above.

The pump 84 is a positive displacement pump which is positioned in the fluid delivery system 16 for delivering water to the thoracic portion 12 while simultaneously removing the same volume water from the left ventricular assembly 14 and vice versa. A suitable pump 84 for use in the present invention is available from Bimba Manufacturing Co., of Monee, Ill., and is sold as part number PT-0981080-MX. This pump 84 includes two pistons (shown schematically in FIG. 9) disposed at each end of a metal cylinder 92. A rack and pinion mechanism is positioned between the pistons. The pinion extends transversely from the midpoint of the cylinder 92 and is engaged by the motor 86 for reciprocating the rack, and therefore the pistons. In one embodiment the motor 86 is a servo motor. A suitable motor for use in the present invention is available from Quicksilver Controls, Inc., of Covina, Calif., and is sold under the trade name SILVERMAX, Part no. QCI-34H-1-E-01.

Figure 7:
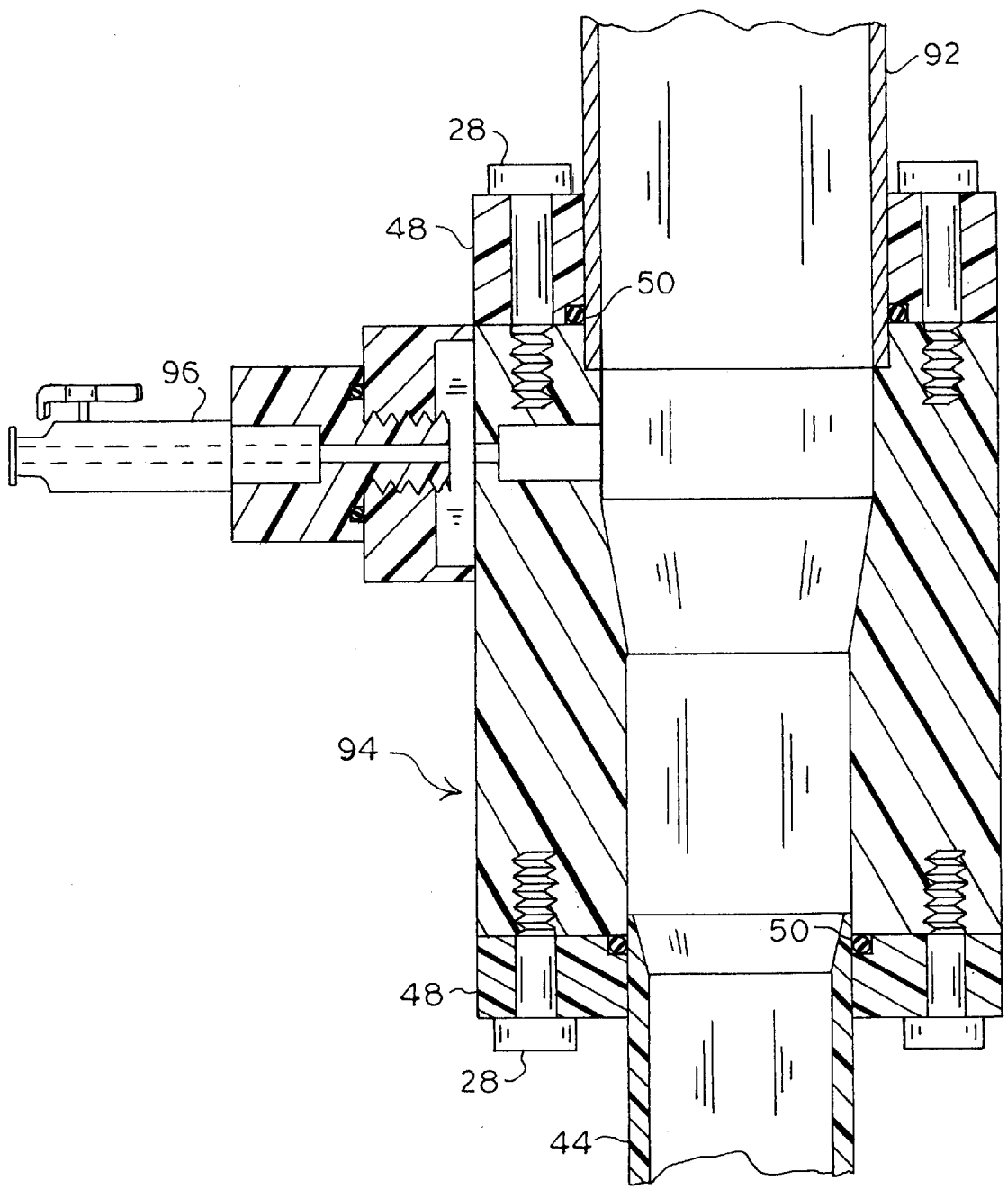
FIG. 7 is a sectional view of a fluid tubing coupling for use in an embodiment of the cardiac phantom according to the present invention.

The upper end of the pump cylinder 92 is sealingly secured to the rear outlet of the crossover 90 of the fluid tubing 80. The lower end of the pump cylinder 92 is received within an enlarged-diameter cylindrical coupling 94 shown in FIG. 7. The upper end of the coupling 94 is sealed to the end of the pump cylinder 92 using the flange 48 and o-ring 50 arrangement described above. The lower end of the coupling 94 sealingly receives the distal end of the upper portion 44 of the fluid delivery tube 38 of the left ventricular assembly 14. Due to the characteristics of the flange 48 and o-ring 50 arrangement used to join the parts of the apparatus, the fluid delivery tube 38 is axially and rotationally movable with respect to the coupling 94 and the top plate 24 of the tank 22. This feature allows the left ventricular assembly 14 to be adjustably positioned within the thoracic portion 12 without disassembling the tank 22.

In use, the cardiac phantom 10 is filled with fluid beginning with the fluid delivery tube 38 and inner cap member 40, 40a of the left ventricular assembly 14. This fluid is commonly referred to as the "blood pool". Fluid is added through a fluid flow valve 96 provided in the wall of the coupling 94. The pistons are positioned at their highest possible point during filling. Fluid may be added until the inner cap member 40, 40a occupies about 60 ml of volume which is the volume of an average human heart during diastole. Next, the space 73 representing the myocardium is filled with fluid through the valve 78 in the top plate 24. The space 73 is filled with sufficient fluid so that the thickness of the space 73 is about 1.4 cm. during systole and about 0.8 cm. during diastole which is consistent with an average human heart. The sufficient amount of fluid is usually about 70 ml. Finally, the thoracic portion 12 is filled through a valve 98 in the top of the crossover 90 of the fluid delivery system 16. The thoracic portion 12 is filled until an air volume of about 50 ml. remains. A syringe is used to remove the excess air through the valve 98 which provides a net negative pressure in the thoracic portion 12. Thus, the entire volume of the thoracic portion 12, left ventricular assembly 14 and fluid delivery system 16 is filled with fluid. Fluid surrounds the left ventricular assembly 14 and simulated non-cardiac thoracic structures 32, 34, 36. All three volumes of fluid are physically separated from one another. Any of the fluid volumes may comprise an active solution having radioactive properties to simulate, for example, thoracic background. The valves 78, 96, 98 are positioned at the highest point of each of the contained fluid volumes for the removal of air bubbles.

In operation, the motor 86 powers the pump 84 thereby reciprocally moving fluid within the left ventricular assembly 12 and, separately, the tank 22 in the thoracic portion 12 in response to movement of the pistons in the cylinder 92. Thus, a "beating" left ventricle is created which is available for medical imaging. Moreover, since the system is closed, the same volume of water is always being moved by pump assembly and there is no net displacement of fluid in the cardiac phantom 10 during contraction and expansion of the ventricular portion 14 and there is no pressure change.

Figure 8:
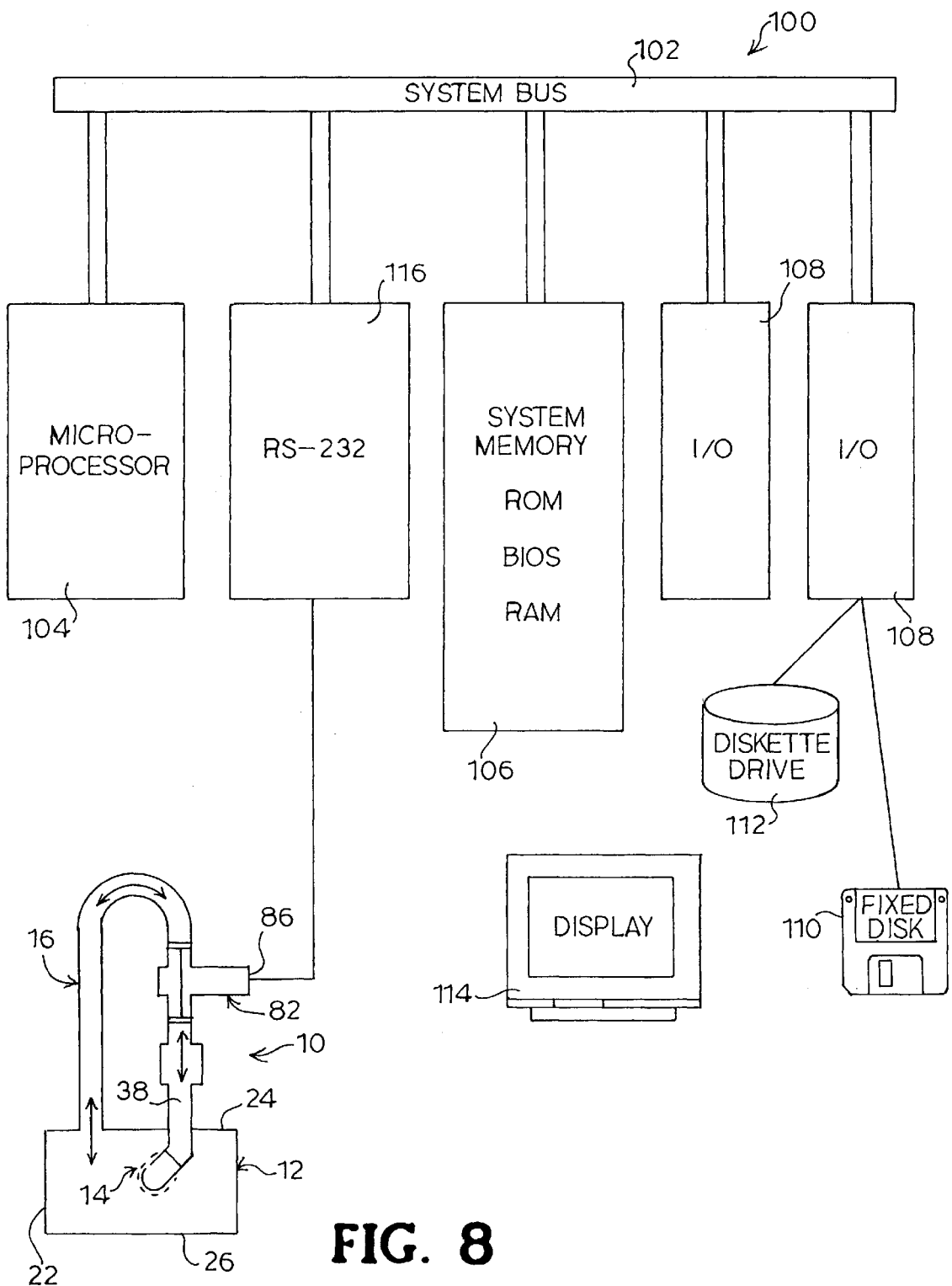
FIG. 8 is a computer system for use in a method for using a cardiac phantom according to the present invention.

The speed and volume delivery of the pump 84 is controlled by software via a control circuit which enables adjustable setting of systolic and diastolic phase lengths of the cardiac phantom 10 for the appropriate cycles, or beats, per minute. Software that can be used to implement the invention resides and runs on one or more computer systems, which in one embodiment, are personal computers, workstations, or servers. FIG. 8 illustrates further detail of a computer system 100 that is implementing part of the invention in this way. System bus 102 interconnects the major components. The system 100 is controlled by a microprocessor 104, which serves as the central processing unit (CPU) for the system. System memory 106 is typically divided into multiple types of memory or memory areas, such as read-only memory (ROM), random-access memory (RAM) and others. If the computer system 100 is an IBM compatible personal computer, the system memory 106 also contains a basic input/output system (BIOS). A plurality of general input/output (I/O) adapters or devices 108 are present. Only two are shown for clarity. The I/O adapters or devices 108 connect to various devices including a fixed disk 110, a diskette drive 112, and a display 114. The computer program instructions for implementing the functions of the cardiac phantom 10 are stored on the fixed disk 110, and are partially loaded into the memory 106 and executed by the microprocessor 104. The system also includes another I/O device, a communications adapter 116 for connection to other devices over an interface, such as a RS232, which in this case allows the computer system to be connected to the motor 86 of the pump assembly 82. It should be noted that the system as shown in FIG. 8 is meant as an illustrative example only. Numerous types of general-purpose computer systems are available and can be used. Available systems include those that run operating systems such as Windows® by Microsoft® and various versions of UNIX®.

Elements of the software program may be embodied in hardware or in software (including firmware, resident software, micro-code, etc.). Furthermore, the invention may take the form of a computer program product on a computer-usable or computer-readable storage medium having computer-usable or computer-readable program code embodied in the medium for use by or in connection with an instruction execution system. Such mediums are shown in FIG. 8 to represent the diskette drive 110 and the hard disk 112. In the context of this specification, a computer-usable or computer-readable medium may be any medium that can contain, store, communicate, propagate, or transport the program for use by or in connection with the instruction execution system, apparatus, or device. The computer-usable or computer-readable medium may be, for example but not limited to, an electronic, magnetic, optical, electromagnetic, infrared, or semiconductor system, apparatus, device, or propagation medium. More specific examples, a nonexhaustive list, of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Various memory types can be used, for example, to store portions of code at the mobile terminal that relate to the invention. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Figure 9:
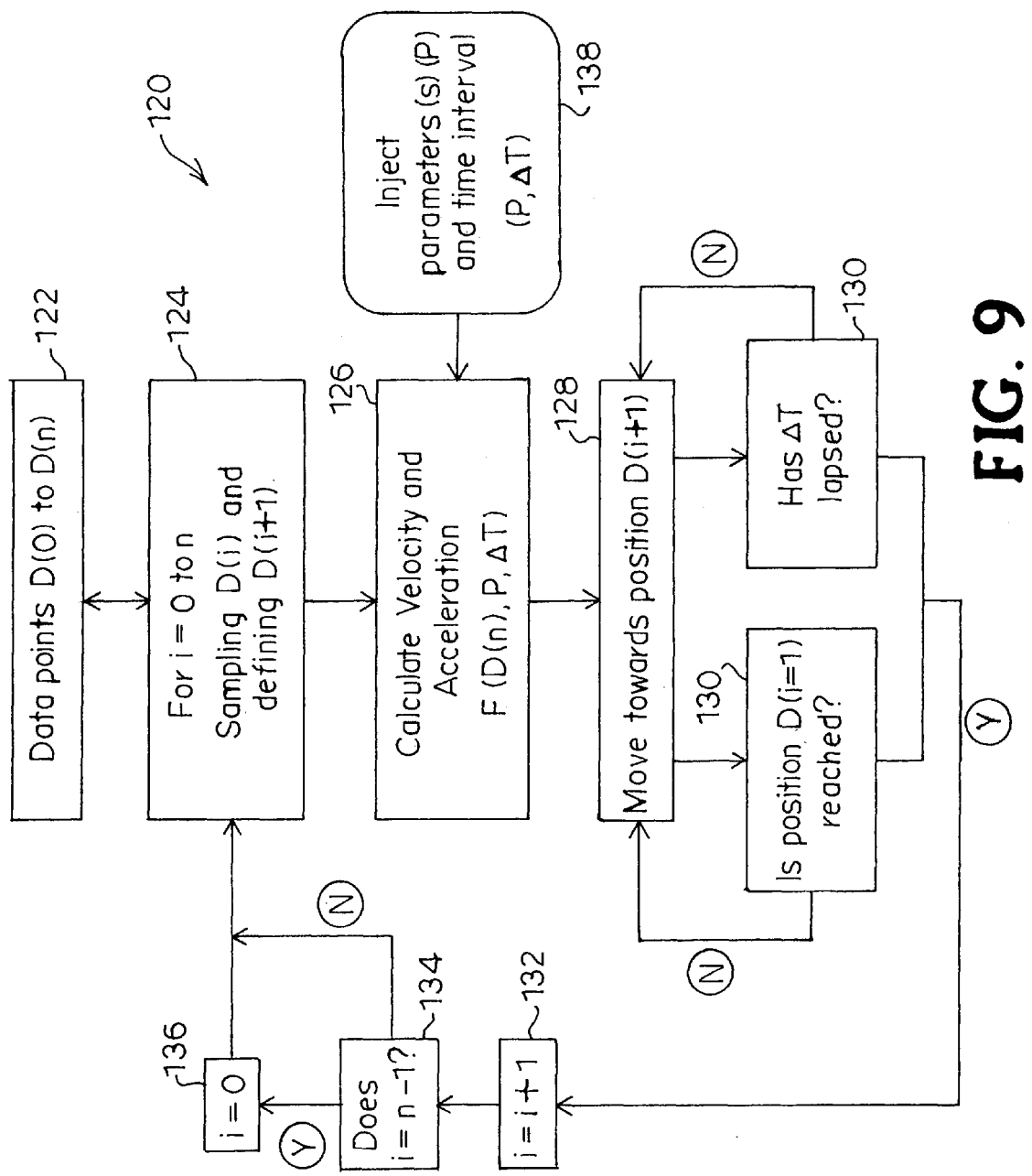
FIG. 9 is a software sequence for use in a method for using a cardiac phantom according to the present invention.
Figure 10:
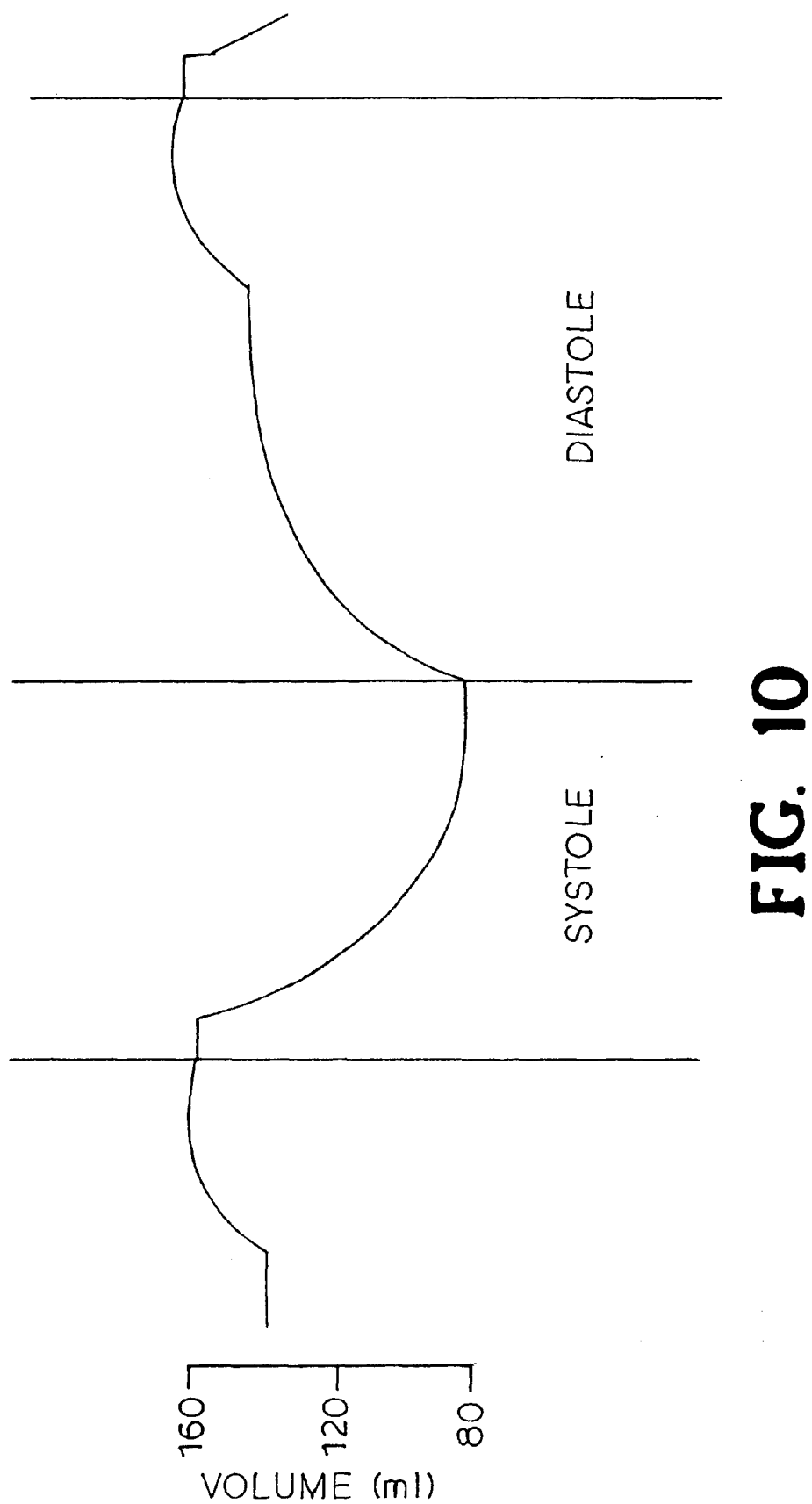
FIG. 10 is a Wiggers' Curve showing volume versus time of a normal left ventricle of a human heart.

In accordance with the present invention, the microprocessor 104 functions to provide a programmed sequence 120 (FIG. 9) which guides the cardiac phantom 10 through a simulated cardiac cycle based on a ventricular volume versus time curve shown in FIG. 10. Referring to FIG. 9, the program sequence 120 begins with the user selecting a number of data points, D(0) to D(n), 122 to be analyzed by a microprocessor. The number of data points which may be selected is not limited. Each data point selected corresponds to a particular ventricular volume at a distinct point in time during the cardiac cycle (FIG. 10), so that when the data points are sequentially connected a ventricular volume versus time curve results.

In the next step, the software samples the position of the pump motor 124. The software then defines a data point, D(i), on the ventricular volume versus time curve based on the position of the motor pinion at a given time. Therefore, the motor position is linked to ventricular volume at a given time, causing a data point, D(i), on the ventricular volume versus time curve 140 to be represented by motor position, (i), in the program sequence. In the same step 124, the software defines a subsequent data point, D(i+1), based the motor position (i+1). This subsequent motor position, (i+1), represents a data point immediately subsequent to the prior data point, D(i), along the ventricular volume versus time curve. After the software 124 defines an initial pump motor position, (i), and a subsequent motor position, (i+1), the software calculates the velocity and acceleration at which the pump motor must advance to arrive at the position, (i+1) 126, while following the curve.

In the next step 128, the software causes the pump motor to move towards the new position, (i+1), that represents the immediately subsequent data point, D(i+1), on the ventricular volume versus time curve. After moving the motor towards its new position, (i+1), the program sequence progresses to a decision step 130 that compares the actual motor position to its expected position at the new position. The decision step 130 determines if the motor moved to its correct position, (i+1), and if the time provided for the motor to reach that correct position has elapsed. If the answer to both questions is NO, the motor will continue to move towards its expected position (i+1). If the answer to either question is YES, the motor is in the correct position, (i+1), or the motor is not in the correct position but the time for it to reach that position has expired, the next step in the sequence considers the motor to have reached the correct position, (i+1) 132.

After the motor reaches its new position at (i+1), the next step 134 is a decisional step asking if i=n−1. If YES, the program continues to the next step 136 which defines the position of the motor, (i), as 0, and the sequence is started again with the motor at the initial position, i=0, 124 which correlates with the initial data point D(0). If NO, (i) does not equal 0 and represents some motor position between 0 and n. The program sequence begins again at step 124 where the new motor position, (i+1), becomes (i).

It is understood that the velocity and acceleration parameters can be changed to mimic dynamic ventricular characteristics including changes in ventricular contraction rate and ejection fraction. The software can be programmed to follow Wiggers' curve or similar normal heart rate curves. Moreover, the software allows the pump to be controlled to simulate in real time all pumping functions and possible clinical conditions of the left ventricular region of the heart, including variations in heart rate, ejection volume, or any abnormal cardiac curve. The cardiac phantom of the present invention is a highly versatile device for testing medical imaging instruments, including those used for SPECT, PET, MRI, x-ray CT, ultrasound, and the like for diagnostic purposes. The left ventricular phantom has a known volume and shape and may be used to calibrate, adjust and detect inaccuracies in virtually any commercially available type of medical imaging instrument or device. Image acquisition can be obtained throughout the normal real time functioning of the heart in diastolic or systolic or in dynamic diastolic-systolic conditions. In particular, the phantom can be used in numerous simulated cardiac situations for providing real time images. Simulated clinical conditions can be used to demonstrate changes in left ventricular ejection fractions and to quantify the left ventricular volumes. When active solution is filled between the walls of the cap members, myocardial abnormalities and defects of various sizes can be simulated, such as myocardial perfusion defects.

The cardiac phantom of the present invention thus provides a useful tool for validating nuclear imaging devices in cardiac imaging studies over a wide range of simulated clinically relevant situations. The validation may be done in real time using the realistic, expansible dynamic left ventricular phantom to simulate the left ventricle of a beating heart. Therefore, the phantom of the present invention has considerable potential as a reference standard in assessing medical imaging devices for analysis of the heart, particularly during real time function.

Although the present invention has been shown and described in considerable detail with respect to only a few exemplary embodiments thereof, it should be understood by those skilled in the art that we do not intend to limit the invention to the embodiments since various modifications, omissions and additions may be made to the disclosed embodiments without materially departing from the novel teachings and advantages of the invention, particularly in light of the foregoing teachings. For example, the cardiac phantom and method described herein for actuating the simulated ventricle can be used with other methods or cardiac phantoms and simulated ventricles, respectively, other than the embodiments disclosed herein. Accordingly, we intend to cover all such modifications, omission, additions and equivalents as may be included within the spirit and scope of the invention as defined by the following claims. In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts, a nail and a crew may be equivalent structures.

We claim:

1. An apparatus for simulating a dynamic cardiac ventricle, comprising:

two concentrically-disposed, fluid-tight, flexible membranes, a closed space defined between the walls of the membranes;

a pump operatively connected to the inner membrane for reciprocally delivering a volume of fluid to the inner membrane to inflate and deflate both membranes in simulating systole and diastole of a heart;

a medium disposed within the closed space defined between the walls of the membranes for maintaining a uniform distance between the walls of the membranes during inflation and deflation, the membranes being open-ended ellipsoids of different diameters;

a rigid fluid tube operatively connecting the pump and the inner membrane, the inner membrane having sufficient diameter to fit over an end of the tube;

a collar for mounting around the joined ends of the tube and inner membrane, the outer membrane having sufficient diameter to fit over the collar;

an o-ring for mounting around the joined collar and outer membrane, the collar having a circumferential groove for receiving the o-ring; and a clamp for mounting around the joined ends of the collar and outer membrane.

2. An apparatus for simulating a dynamic cardiac ventricle, comprising:

two concentrically-disposed, fluid-tight, flexible membranes, a closed space defined between the walls of the membranes;

a pump operatively connected to the inner membrane for reciprocally delivering a volume of fluid to the inner membrane to inflate and deflate both membranes in simulating systole and diastole of a heart;

a medium disposed within the closed space defined between the walls of the membranes for maintaining a uniform distance between the walls of the membranes during inflation and deflation, the membranes being cylinders having different diameters and closed at one end;

a rigid fluid tube operatively connecting the pump and the inner membrane, the inner membrane having sufficient diameter to fit over an end of the tube, a collar for mounting around the joined ends of the tube and inner membrane, the outer membrane having sufficient diameter to fit over the collar, an o-ring for mounting around the joined collar and outer membrane, the collar having a circumferential groove for receiving the o-ring, and a clamp for mounting around the joined ends of the collar and outer membrane.

3. An apparatus for simulating a cardiac ventricle as recited in claim 2, wherein the closed end of the cylindrical membranes comprises:

a plug, the inner membrane having sufficient diameter to fit over at least a portion of the plug, a second collar for mounting around the joined portion of the plug and inner membrane, the outer membrane having sufficient diameter to fit over the collar, a second o-ring for mounting around the joined second collar and outer membrane, the second collar having a circumferential groove for receiving the second o-ring, and a second clamp for mounting around the joined ends of the second collar and outer membrane.

4. An apparatus for simulating a cardiac ventricle as recited in claim 3, further comprising means for providing support along the longitudinal axis of the membranes.

5. An apparatus for simulating a cardiac ventricle as recited in claim 4, wherein the longitudinal support means comprises a second plug received within the end of the fluid tube, the second plug having at least one opening for the passage of fluid between the tube and inner membrane, and a connecting member joining the plug at the closed end of the inner membrane and the second plug.

6. An apparatus for simulating a cardiac ventricle as recited in claim 5, wherein the connecting member is hollow for receiving fluid.

7. An apparatus for simulating a cardiac ventricle as recited in claim 4, wherein the plug has a peripheral flange extending beyond the periphery of the outer membrane, the longitudinal support means comprising at least two spaced shoulders on the tube adjacent the end of the tube and extending beyond the periphery of the outer membrane, and a plate mounted to each shoulder, the plates extending longitudinally to engage the flange.

8. A phantom for evaluation of a medical imaging system, the phantom comprising:

a closed container of fluid;

a simulated dynamic cardiac ventricle disposed within the container, the cardiac ventricle including two concentrically-disposed, fluid-tight, flexible membranes, a closed space defined between the walls of the membranes, and a medium disposed within the closed space defined between the walls of the membranes for maintaining a uniform distance between the walls of the membranes during inflation and deflation; and a fluid delivery system including a pump between the container of fluid and the inner membrane for reciprocating the same volume of fluid between the container and the inner membrane to inflate and to deflate both membranes in simulating systole and diastole of a heart, so that there is no net displacement of fluid in the phantom during contraction and expansion of the ventricle and there is no pressure change.

9. A phantom for evaluation of a medical imaging system as recited in claim 8, wherein the fluid delivery system further comprises a rigid fluid tube for connecting one port of the pump and the inner membrane.

10. A phantom for evaluation of a medical imaging system as recited in claim 8, wherein the medium is a fluid.

11. A phantom for evaluation of a medical imaging system as recited in claim 10, wherein at least one of the fluid in the container, the volume of fluid, or the medium fluid is a radioisotope.

12. A phantom for evaluation of a medical imaging system as recited in claim 8, wherein the medium is foam.

13. A phantom for evaluation of a medical imaging system as recited in claim 12, wherein the foam simulates a heart defect.

14. A phantom for evaluation of a medical imaging system as recited in claim 12, wherein the foam is an open-cell foam for the uptake of liquid radioactive tracer material.

15. A phantom for evaluation of a medical imaging system, the phantom comprising:

a closed container of fluid;

a simulated dynamic cardiac ventricle disposed within the container, the cardiac ventricle including two concentrically-disposed, fluid-tight, flexible membranes, a closed space defined between the walls of the membranes, and a medium disposed within the closed space defined between the walls of the membranes for maintaining a uniform distance between the walls of the membranes during inflation and deflation;

a fluid delivery system including a pump between the container of fluid and the inner membrane for reciprocating a volume of fluid between the container and the inner membrane to inflate and deflate both membranes in simulating systole and diastole of a heart, the membranes being open-ended ellipsoids of different diameters;

a rigid fluid tube for connecting one port of the pump and the inner membrane, the inner membrane having sufficient diameter to fit over an end of the tube;

a collar for mounting around the joined ends of the tube and inner membrane, the outer membrane having sufficient diameter to fit over the collar;

an o-ring for mounting around the joined collar and outer membrane, the collar having a circumferential groove for receiving the o-ring: and a clamp for mounting around the joined ends of the collar and outer membrane.

16. A phantom for evaluation of a medical imaging system, the phantom comprising:

a closed container of fluid;

a simulated dynamic cardiac ventricle disposed within the container, the cardiac ventricle including two concentrically-disposed, fluid-tight, flexible membranes, a closed space defined between the walls of the membranes, and a medium disposed within the closed space defined between the walls of the membranes for maintaining a uniform distance between the walls of the membranes during inflation and deflation;

a fluid delivery system including a pump between the container of fluid and the inner membrane for reciprocating a volume of fluid between the container and the inner membrane to inflate and deflate both membranes in simulating systole and diastole of a heart, the membranes being cylinders having different diameters and closed at one end;

a rigid fluid tube for connecting one port of the pump and the inner membrane, the inner membrane having sufficient diameter to fit over an end of the tube;

a collar for mounting around the joined ends of the tube and inner membrane, the outer membrane having sufficient diameter to fit over the collar;

an o-ring for mounting around the joined collar and outer membrane, the collar having a circumferential groove for receiving the o-ring; and a clamp for mounting around the joined ends of the collar and outer membrane.

17. A phantom for evaluation of a medical imaging system as recited in claim 13, wherein the closed end of the cylindrical membranes comprises:

a plug, the inner membrane having sufficient diameter to fit over at least a portion of the plug, a second collar for mounting around the joined portion of the plug and inner membrane, the outer membrane having sufficient diameter to fit over the collar, a second o-ring for mounting around the joined second collar and outer membrane, the second collar having a circumferential groove for receiving the second o-ring, and a second clamp for mounting around the joined ends of the second collar and outer membrane.

18. A phantom for evaluation of a medical imaging system as recited in claim 17, further comprising a second plug received within the end of the fluid tube, the second plug having at least one opening for the passage of fluid between the tube and inner membrane, and a connecting member joining the plug at the closed end of the inner membrane and the second plug.

19. A phantom for evaluation of a medical imaging system as recited in claim 17, wherein the plug has a peripheral flange extending beyond the periphery of the outer membrane, and further comprising at least two spaced shoulders on the tube adjacent the end of the tube and extending beyond the periphery of the outer membrane, and a plate mounted to each shoulder, the plates extending longitudinally to engage the flange.

* * * * *